(12) United States Patent
Kaushik et al.

(10) Patent No.: US 10,012,645 B2
(45) Date of Patent: Jul. 3, 2018

(54) RAPID ZIKA VIRUS DETECTION USING NANO-ENABLED ELECTROCHEMICAL SENSING SYSTEM

(71) Applicants: Ajeet Kaushik, Doral, FL (US); Madhavan Nair, Coral Gables, FL (US)

(72) Inventors: Ajeet Kaushik, Doral, FL (US); Madhavan Nair, Coral Gables, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days.

(21) Appl. No.: 15/246,065

(22) Filed: Aug. 24, 2016

(65) Prior Publication Data

US 2018/0059099 A1    Mar. 1, 2018

(51) Int. Cl.
*G01N 33/543* (2006.01)
*G01N 33/569* (2006.01)
*G01N 33/553* (2006.01)
*G01N 27/327* (2006.01)

(52) U.S. Cl.
CPC ..... *G01N 33/5438* (2013.01); *G01N 27/3278* (2013.01); *G01N 33/553* (2013.01); *G01N 33/56983* (2013.01); *G01N 2333/185* (2013.01)

(58) Field of Classification Search
CPC ......... G01N 33/5438; G01N 33/56983; G01N 33/553; G01N 27/3278
See application file for complete search history.

(56) References Cited

U.S. PATENT DOCUMENTS

| | | | |
|---|---|---|---|
| 6,670,115 B1* | 12/2003 | Zhang | G01N 33/5438 204/193 |
| 9,777,337 B2* | 10/2017 | Schulze | C12Q 1/689 |
| 2002/0090649 A1* | 7/2002 | Chan | B01J 19/0046 435/7.1 |

(Continued)

OTHER PUBLICATIONS

Cohen, Adam E.; Kunz, Roderick R., "Large-area interdigitated array microelectrodes for electrochemical sensing." *Sensors and Actuators B*, Jan. 2000, 62:23-29.

(Continued)

*Primary Examiner* — Melanie Yu Brown
(74) *Attorney, Agent, or Firm* — Saliwanchik, Lloyd & Eisenschenk

(57) ABSTRACT

The subject invention provides materials and methods for detecting Zika virus. Specific embodiments provide an electrochemical immunosensing device and the methods of making and using the same for detecting Zika virus with exceptionally low detection limit. In some embodiments, the immunosensing device is capable of detecting picomolar (pM) level of Zika virus present in a sample by employing immunosensors functionalized with Zika virus binding ligands such as monoclonal Zika virus antibodies and Zika non-structural proteins. In an exemplary embodiment, the immunosensing device can be integrated with microelectronics to be adopted as point-of-care sensing systems. Advantageously, technologies provided herein offer rapid, on-site biosensing methods for the accurate detection of diseases caused by Zika virus.

17 Claims, 2 Drawing Sheets

(56) References Cited

U.S. PATENT DOCUMENTS

| | | | | |
|---|---|---|---|---|
| 2004/0058457 A1* | 3/2004 | Huang | | B82Y 5/00 |
| | | | | 436/524 |
| 2005/0059105 A1* | 3/2005 | Alocilja | | G01N 33/569 |
| | | | | 435/7.32 |
| 2005/0112544 A1* | 5/2005 | Xu | | C12M 23/12 |
| | | | | 435/4 |
| 2006/0188894 A1* | 8/2006 | Chen | | C07K 16/1081 |
| | | | | 435/5 |
| 2009/0243584 A1* | 10/2009 | Zhang | | B81C 1/00031 |
| | | | | 324/71.1 |
| 2011/0024309 A1* | 2/2011 | Lee | | G01N 27/3276 |
| | | | | 205/792 |
| 2014/0274762 A1* | 9/2014 | Manuguerra | | G01N 33/6845 |
| | | | | 506/9 |
| 2015/0247816 A1* | 9/2015 | Bhansali | | G01N 27/3275 |
| | | | | 205/782 |
| 2015/0282743 A1* | 10/2015 | Etzkorn | | G01N 27/3271 |
| | | | | 600/345 |
| 2017/0059561 A1* | 3/2017 | Bhansali | | G01N 33/5438 |
| 2017/0107565 A1* | 4/2017 | Marinero-Caceres | | G01N 27/3276 |
| 2017/0298119 A1* | 10/2017 | Wollacott | | C07K 16/10 |

OTHER PUBLICATIONS

Iwasaki, Yuzuru; Morita, Masao, "Electrochemical Measurements with Interdigitated Array Microelectrodes." *Current Separations*, 1995, 14:1-8.

Kaushik, A. et al., "A label-free electrochemical immunosensor for beta-amyloid detection," *Analytical Methods*, 2016, 8: 6115-6120, DOI: 10.1039/c6ay01910b.

Kaushik, A. et al., "Electrochemical sensing method for point-of-care cortisol detection in human immunodeficiency virus-infected patients." *International Journal of Nanomedicine*, 2015, 10: 1-9.

Pasha, S. K., et al., "Electrochemical Immunosensing of Saliva Cortisol." *Journal of the Electrochemical Society*, 2014, 161(2): B3077-B3082, DOI: 10.1149/2.017402jes.

\* cited by examiner

RAPID ZIKA VIRUS DETECTION USING NANO-ENABLED ELECTROCHEMICAL SENSING SYSTEM

BACKGROUND OF INVENTION

Recent advancements in sensing technology have enabled biosensors to detect specific biological target analytes with extremely low detection limits such as, for example, picomolar (pM) and femtomolar (fM) levels. Nano-enabled biosensors, with their application-specific design and packaging, can be readily utilized in point-of-care (POC) sensing systems that generate bioinformatics useful for diagnosing and monitoring various diseases.

Though Zika virus, a mosquito-borne pathogen, often directly causes only mild symptoms, it has been recently linked to occurrences of microcephaly when the virus is passed from a pregnant woman to her fetus. Due to the fact that Zika virus is difficult to identify and monitor at early stages, international health agencies have declared a state of emergency in areas heavily affected by Zika virus.

Currently, enzyme-linked immunosorbent assay (ELISA) and real time-polymerase chain reaction (RT-PCR) are two major laboratory methods available for detecting Zika virus. These methods can be used to detect the virus, for example, within 3-10 days following the onset of symptoms. However, the ELISA test adopted for detecting Zika virus has limitations due to cross reactivity of the antibodies with other species of the *Flavivirus* genus such as, for example, dengue virus. Also, ELISA is cumbersome for healthcare workers to carry and utilize. Because these methods are typically carried out in laboratories only, the turn-around time for a confirmed laboratory diagnostics results can take up to days, causing significant delays in diagnosis and treatment. In addition, these test methods are unable to detect Zika virus at low detection limits, which can result in misidentification of the viral infection at an early stage.

Therefore, developing a cost-effective, rapid, sensitive, and selective immunosensor for detecting Zika virus is of great importance in view of the significant Zika outbreak in many areas.

BRIEF SUMMARY

The subject invention provides devices and methods for detecting Zika virus. Specific embodiments provide an electrochemical immunosensing device and the methods of making and using the same for detecting Zika virus with very low detection limit.

In some embodiments, the immunosensing device is capable of detecting picomolar (pM) levels of Zika virus present in a sample by employing immunosensors functionalized with Zika virus binding ligands such as monoclonal Zika virus antibodies and Zika non-structural proteins.

In some embodiments, the detection of Zika virus can be accomplished in 40 minutes or less without requiring the use of laboratory testing. In an exemplary embodiment, the immunosensing device can be integrated with microelectronics to be adopted as point-of-care sensing systems.

Advantageously, technologies provided herein offer rapid, on-site biosensing methods for the accurate detection of diseases caused by Zika virus without requiring, for example, extensive power supply or the need for a laboratory testing facility.

DETAILED DISCLOSURE

Figure 1:
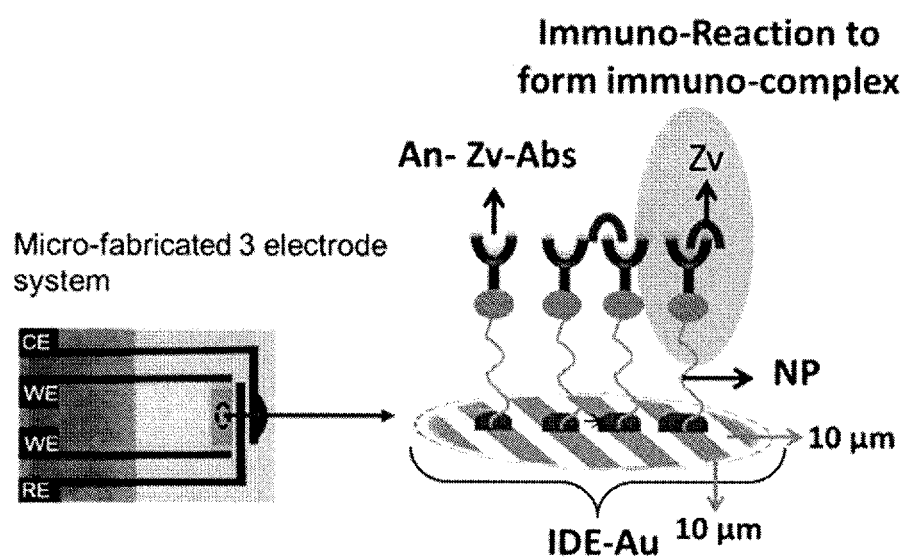
FIG. 1 is a schematic of an exemplary embodiment of the immunosensing device of the subject invention. Zika virus (Zv), anti-Zika virus antibody (An-Zv-Abs), interdigitated electrode of gold (IDE-Au), and nanostructured platform (NP) are various components of the sensing device.
Figure 2:
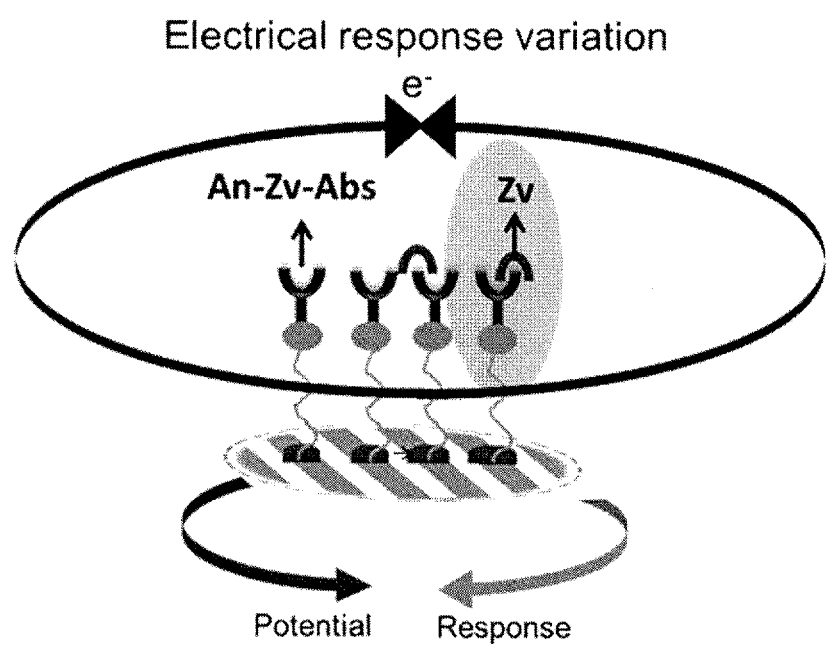
FIG. 2 illustrates the working principle of an exemplary embodiment of the immunosensing device of the subject invention.

The subject invention provides devices and methods for detecting Zika virus. Specific embodiments provide an electrochemical immunosensing device and the methods of making and using the same for detecting Zika virus with very low detection limit.

In one aspect, the subject invention provides an immunosensing substrate whose surface is configured to comprise an array of interdigitated electrodes (IDEs), which are further functionalized with one or more nanostructured platforms (NPs) having immobilized thereon biomarkers for zika virus.

In some embodiments, the immunosensing substrate comprises a plurality of parallel microband arrays of interdigitated electrodes, with each set of electrodes potentiostated individually. As such, one electrode is held at a potential to drive an oxidation reaction, while the adjacent electrode is held at a potential to drive a reduction reaction. Electroactive species generated at one electrode can diffuse across a small gap, with a width typically no more than 10 μm, and are subsequently converted back to their original charge.

This cyclic exchange of charges between two adjacent microelectrodes fabricated in an interdigitated pattern can greatly amplify the magnitude of the current output of the overall device.

As a result, sensors comprising IDEs have improved detection sensitivity as a result of the increased current output generated by the microfabricated pattern (A. E. Cohen and R. R. Kunz, Sensors and Actuators B: Chemical, 62, 23 (2000); Y. Iwasaki and M. Morita, Current Separations, 14, 1 (1995)). Advantageously, the immunosensing substrate comprising IDEs as provided herein is capable of achieving a much lower detection limit such as, for example, on the orders of picomolar (pM) or even femtomolar (fM).

In some embodiments, the IDEs comprise one or more materials such as, for example, gold, platinum, and glassy carbon. In an exemplary embodiment, the IDEs comprise gold.

In order to further increase the detection sensitivity, embodiments of the subject invention provide that the effect of the Zika virus binding ligands immobilized onto the immunosensing substrate can be enhanced by functionalizing the immunosensing substrate prior to immobilization. In some embodiments, surface functionalization is achieved by chemically modifying the immunosensing substrate with one or more of the following nanostructured platforms (NPs): self-assembled monolayers (SAMs), metallic nanoparticles, metal oxide nanoparticles, functionalized nanopolymers, hybrid nanocomposites, and nanostructured thin films.

Other suitable platforms with nanoscopic structures and appropriate chemical functionalities can also be employed to construct the immunosensing substrate. In some embodiments, NPs provided herein can be further functionalized by one or more of a variety of chemical moieties including, for example, peptides, proteins, therapeutic agents (i.e., drugs), and molecular taggants. In certain embodiments, the NPs carry electrostatic charges at the surface.

Nanoparticles, nanopolymers, and nanocomposites are exemplary structures having dimensions on the order of nanometers with various chemical and physical properties tailored to specific applications. Self-assembled monolayers (SAMs) are highly ordered molecular assemblies that form spontaneously by chemisorption of functionalized molecules on a variety of substrates such as metals, silicon, and glass. These molecules organize themselves laterally, most commonly via van der Waals interactions between long aliphatic chains. The thickness of a typical SAM is between about 10 and about 40 Å.

In an exemplary embodiment, the immunosensing substrate provided herein comprises a silane-based SAM that chemically links the gold IDEs with binding ligands for the Zika virus. Advantageously, the selection of an appropriate NP can increase the loading of binding ligands capable of binding with the virus of interest via electrostatic or chemical bonds, resulting in wider range of linear detection, lower detection limit, and higher sensitivity.

In some embodiments, the subject invention provides devices and methods for detecting viruses belonging to the family Flaviviridae, which includes but is not limited to, Zika virus, dengue virus, yellow fever virus, West Nile virus, Japanese encephalitis virus, tick-borne encephalitis virus, Kunjin virus, Murray Valley encephalitis virus, St. Louis encephalitis virus, Omsk hemorrhagic fever virus, bovine viral diarrhea virus, Gadgets Gully virus, Kyasanur Forest disease virus, Langat virus, Louping ill virus, Powassan virus, Royal Farm virus, Karshi virus, Kadamvirus, Meaban virus, Saumarez Reef virus, Tyuleniy virus, Aroa virus, Bussuquara virus, Iguape virus, Naranjal virus, Kedougou virus, Cacipacore virus, Koutango virus, Alfuy virus, Usutu virus, Yaounde virus, Kokobera virus, Stratford virus, Bagaza virus, Ilheus virus, Rocio virus, Israeli turkey meningoencephalomyelitis virus, Ntaya virus, Tembusu virus, Sponweni virus, Banzi virus, Bouboui virus, Edge Hill virus, Jugra virus, Potiskum virus, Saboya virus, Sepik virus, Ugandavirus, Wesselsbron virus, Entebbe bat virus, Sokoluk virus, Yokose virus, Apoi virus, Cowbone Ridge virus, Jutiapa virus, modoc virus, Sal Vieja virus, San Perlita virus, Bukalasa bat virus, Carey Island virus, Dakar bat virus, Mantana myotis leukoencephalitis virus, Batu Cave virus, Phnom Penh bat virus, Rio Bravo virus, Cell fusing agent virus, Tamana bat virus and Hepatitis C virus, especially Zika virus, dengue virus, yellow fever virus, West Nile virus, Japanese encephalitis virus, tick-borne encephalitis virus, Kunjin virus, Murray Valley encephalitis virus, St. Louis encephalitis virus, Omsk hemorrhagic fever virus, bovine viral diarrhea virus, and Hepatitis C virus.

In exemplary embodiments, the subject invention pertains to the detection of Zika virus by providing devices comprising binding ligands for Zika virus in particular. As used herein, binding ligands are defined as biological molecules capable of recognizing a target analyte and include, but are not limited to, peptides, proteins (e.g., enzymes), lipids, DNAs, RNAs, aptamers, and antibodies.

In preferred embodiments, the subject invention provides an immunosensing substrate immobilized with a biomarker selected from monoclonal antibodies specific to non-structural protein 1 (NS-1) of Zika virus and monoclonal antibodies specific to Zika virus' envelope protein. NS-1, an essential glycoprotein for the replication of Zika virus, is expressed on the Zika-infected cell surface and secreted into the extracellular space in which it acts as an antagonist to complement pathway activation.

In some embodiments, the immunosensing substrate provided herein is the working electrode of an electrochemical sensing device that further comprises a counter electrode and a reference electrode. In preferred embodiments, the immunosensing substrate as the working electrode of an electrochemical sensing device can be integrated with microelectronics for point-of-care (POC) applications to detect target diseases, manage treatments, and promote personalized healthcare regimes. In an exemplary embodiment, the electrochemical sensing device comprising the immunosensing substrate can be integrated with one or more microelectromechanical systems (MEMS) and miniaturized potentiostats.

MEMS herein broadly refers to small, mechanical devices constructed using techniques traditionally associated with integrated circuit wafer processing. Conventionally, MEMS devices generally range in size from 20 μm to 1 mm and comprise much smaller components ranging between 1 μm and 100 μm in size. A typical MEMS device comprises a central unit that processes data (e.g., a microprocessor) and several components that interact with the surroundings, such as a sensing component. Exemplary MEMS devices include, but are not limited to, miniaturized gears, levers, cantilevers, and springs. The specific MEMS devices that can be employed for the electrochemical sensing devices provided herein can vary in accordance with the target POC applications.

A potentiostat is an electronic hardware required to control a three-electrode (e.g., working electrode, counter electrode, and reference electrode) electrochemical cell and carry out electroanalytical experiments. In some embodiments provided herein, a potentiostat measures the current flow between the working electrode and counter electrode by controlling the voltage difference between the working electrode and the reference electrode. Any known potentiostat suitable for integration with a three-electrode cell comprising IDEs and MEMS devices can be adapted for use in the present invention, and those skilled in the art would recognize that the configuration of the potentiostat can be varied according to the target POC applications.

POC testing is particularly desirable for today's healthcare needs because it rapidly delivers results to medical practitioners and enables faster consultation. Early diagnosis allows a practitioner to begin treatment sooner, thus avoiding deterioration of a patient's condition. Examples of existing POC analyses include, but are not limited to, tests for viral diseases, glucose, drugs of abuse, serum cholesterol, pregnancy, and ovulation. Advantageously, exemplary embodiments involving highly effective immunosensing devices integrated with MEMS and miniaturized potentiostats can enable POC testing of viral diseases caused by a *Flavivirus* such as, for example, Zika virus without requiring elaborate laboratory testing equipment and apparatus.

The sensitivity of a biosensor is influenced by the selected electrochemical transduction method by which the sensing signals are detected and subsequently processed. In accordance with embodiments provided herein, biologically suitable transduction methods for monitoring and detecting a target analyte such as Zika virus include, for example, cyclic voltammetry (CV, whose output is in terms of current) and electrochemical impedance spectroscopy (EIS, whose output is in terms of impedance or resistance). In certain embodiments of the subject invention, both CV and EIS can be used to detect Zika virus using the immunosensing substrate provided herein.

In some embodiments, a variable selected from voltage, current, and frequency is applied to the sensing device, and depending upon the variable selected, changes in electrical response such as, for example, current or resistance, can be monitored in the device and used to quantify the amount of Zika virus present in the sample.

Other analytical methods are also available for measuring the electrochemical response of the device. Non-limiting examples include chronoamperometry, chronovoltammetry, and differential pulse voltammetry. Persons of ordinary skill in the art would recognize that other suitable electrochemical techniques, now known or hereafter developed, can also be employed to detect a target antigen using the immunosensing devices provided herein.

In another aspect, the subject invention provides methods of using an immunosensing device for detecting Zika virus, that comprises contacting the immunosensing substrate with a sample of interest, allowing the binding ligands on the substrate to interact with any Zika virus present in the sample, monitoring changes in current response output by the device as the target analyte binds with the binding ligands, and comparing the detection results to a calibration curve to determine the amount of Zika virus present. In some embodiments, the calibration curve is established by measuring the amount of Zika virus present in a known sample. In an exemplary embodiment, the detection of Zika virus can be accomplished in about 40 minutes or less without requiring any laboratory-based testing.

In one embodiment, the subject invention comprises a method of detecting Zika virus as a target analyte, comprising:

a) providing an electrochemical sensing device comprising a working electrode, a counter electrode, and a reference electrode, characterized in that the working electrode is an immunosensing substrate characterized in that the surface of the substrate comprises gold and is configured to comprise an array of interdigitated electrodes, the interdigitated electrodes being functionalized with one or more nanostructure platforms selected from self-assembled monolayers (SAMs), metallic nanoparticles, metal oxide nanoparticles, functionalized nanopolymers, hybrid nanocomposites, and nanostructured thin films, and further immobilized with binding ligands specific to Zika virus and/or Zika virus-infected cells;

b) contacting the immunosensing substrate with a biological sample, characterized in that the biological sample is a human physiological fluid selected from blood, plasma, serum, saliva, urine, and tears;

c) applying voltage, current, or frequency to the sensing device;

d) monitoring changes in electrical response of the sensing device as Zika virus or Zika virus-infected cells bind with their binding ligands; and e) quantifying the amount of Zika virus present in the biological sample by comparing the measured current response with a pre-determined calibration curve.

The changes can be, for example, in the form of current or resistance.

The sample can be, for example, human physiological fluids, cell cultures, and environmental samples. In specific embodiments, the sample is a human physiological fluid selected from blood, plasma, serum, saliva, urine, and tears.

Any suitable method for contacting the substrate with the sample may be used. For example, suitable methods include rinsing, dipping, or immersing the immunosensing substrate in a sample, passing a stream comprising the sample over the substrate, or a combination thereof. In a preferred embodiment, the sample is placed in contact with the substrate for about 30 minutes. Any known method of contacting a substrate with a sample can be adapted for use in the present invention, and those skilled in the art would recognize that the duration of immersion can be varied within a reasonable range.

Advantageously, technologies provided herein offer rapid, on-site biosensing methods for the accurate detection of diseases caused by Zika virus without requiring extensive power supply or the need for a laboratory testing facility.

The examples and embodiments described herein are for illustrative purposes only and various modifications or changes in light thereof will be suggested to persons skilled in the art and are included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

All patents, patent applications, provisional applications, and publications referred to or cited herein (including those in the "References" section) are incorporated by reference in their entirety, including all figures and tables, to the extent they are not inconsistent with the explicit teachings of this specification.

We claim:

1. A method of detecting Zika virus as a target analyte, comprising:

a) providing an electrochemical sensing device comprising a working electrode, a counter electrode, and a reference electrode, the working electrode being an immunosensing substrate having a surface comprising gold and an array of interdigitated electrodes, the interdigitated electrodes being functionalized with one or more nanostructure platforms (NPs) selected from self-assembled monolayers (SAMs), metallic nanoparticles, metal oxide nanoparticles, functionalized nanopolymers, hybrid nanocomposites, and nanostructured thin films, and one or more NPs further being immobilized with binding ligands specific to Zika virus and/or Zika virus-infected cells;

b) contacting the immunosensing substrate with a biological sample, the biological sample being a human physiological fluid selected from blood, plasma, serum, saliva, urine, and tears;

c) applying a frequency to the sensing device;

d) monitoring changes in resistance response of the sensing device as Zika virus or Zika virus-infected cells bind with their binding ligands; and e) quantifying the amount of Zika virus present in the biological sample by comparing the measured resistance response with a pre-determined calibration curve.

2. The method according to claim 1, wherein the electrochemical sensing device is further integrated with one or more components selected from microelectromechanical systems (MEMS) and miniaturized potentiostats.

3. The method according to claim 1, wherein the nanostructures are further functionalized with one or more chemical moieties selected from peptides, proteins, therapeutic agents, and molecular taggants.

4. The method according to claim 1, wherein the binding ligands are selected from monoclonal antibodies specific to non-structural protein 1 (NS-1) of Zika virus and monoclonal antibodies specific to Zika virus' envelope protein.

5. The method according to claim 1, wherein the interdigitated electrodes comprise one or more materials selected from gold, platinum, and glassy carbon.

6. The method according to claim 5, wherein the interdigitated electrodes comprise gold.

7. The method according to claim 1, wherein the nanostructure platforms are self-assembled monolayers (SAMs).

8. The method according to claim 1, which is capable of detecting Zika virus present in concentrations on the order of picomolar (pM) or less.

9. The method according to claim 1, wherein the nanostructures carry electrostatic charges at the surface.

10. A method of detecting Zika virus as a target analyte, comprising:
  a) providing an electrochemical sensing device comprising a working electrode, a counter electrode, and a reference electrode, the working electrode being an immunosensing substrate having a surface comprising gold and an array of interdigitated electrodes, the interdigitated electrodes being functionalized with self-assembled monolayers (SAMs), and further immobilized with binding ligands specific to Zika virus and/or Zika virus-infected cells, wherein the interdigitated electrodes comprises gold, and the binding ligands are selected from monoclonal antibodies specific to non-structural protein 1 (NS-1) of Zika virus and monoclonal antibodies specific to Zika virus' envelope protein;
  b) contacting the immunosensing substrate with a biological sample, the biological sample being a human physiological fluid selected from blood, plasma, serum, saliva, urine, and tears;
  c) applying a frequency to the sensing device;
  d) monitoring changes in resistance response of the sensing device as Zika virus or Zika virus-infected cells bind with their binding ligands; and
  e) quantifying the amount of Zika virus present in the biological sample by comparing the measured resistance response with a pre-determined calibration curve;
  the method being capable of detecting Zika virus present in concentrations on the order of picomolar (pM).

11. A method of detecting Zika virus as a target analyte, comprising:
  a) providing an electrochemical sensing device comprising two working electrodes, a counter electrode, and a reference electrode, the two working electrodes being immunosensing substrates having surfaces comprising gold and an array of interdigitated electrodes, the interdigitated electrodes being functionalized with one or more nanostructure platforms selected from self-assembled monolayers (SAMs), metallic nanoparticles, metal oxide nanoparticles, functionalized nanopolymers, hybrid nanocomposites, and nanostructured thin films, and further immobilized with binding ligands specific to Zika virus and/or Zika virus-infected cells;
  b) contacting the immunosensing substrate with a biological sample, the biological sample being a human physiological fluid selected from blood, plasma, serum, saliva, urine, and tears;
  c) applying a frequency to the sensing device;
  d) monitoring changes in resistance response of the sensing device as Zika virus or Zika virus-infected cells bind with their binding ligands; and
  e) quantifying the amount of Zika virus present in the biological sample by comparing the measured resistance response with a pre-determined calibration curve.

12. The method according to claim 11, wherein the electrochemical sensing device is further integrated with one or more components selected from microelectromechanical systems (MEMS) and miniaturized potentiostats.

13. The method according to claim 11, wherein the nanostructures are further functionalized with one or more chemical moieties selected from peptides, proteins, therapeutic agents, and molecular taggants.

14. The method according to claim 11, wherein the binding ligands are selected from monoclonal antibodies specific to non-structural protein 1 (NS-1) of Zika virus and monoclonal antibodies specific to Zika virus' envelope protein.

15. The method according to claim 11, wherein the interdigitated electrodes comprise gold.

16. The method according to claim 11, wherein the nanostructure platforms are self-assembled monolayers (SAMs).

17. The method according to claim 11, which is capable of detecting Zika virus present in concentrations on the order of picomolar (pM).

* * * * *